Figure 1:
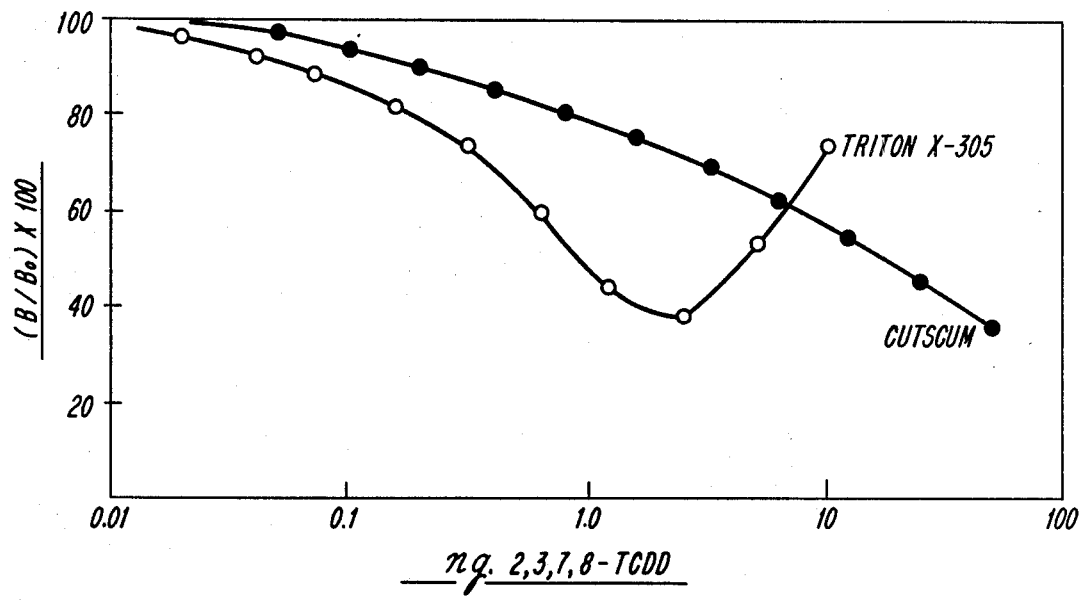
Figure 2:
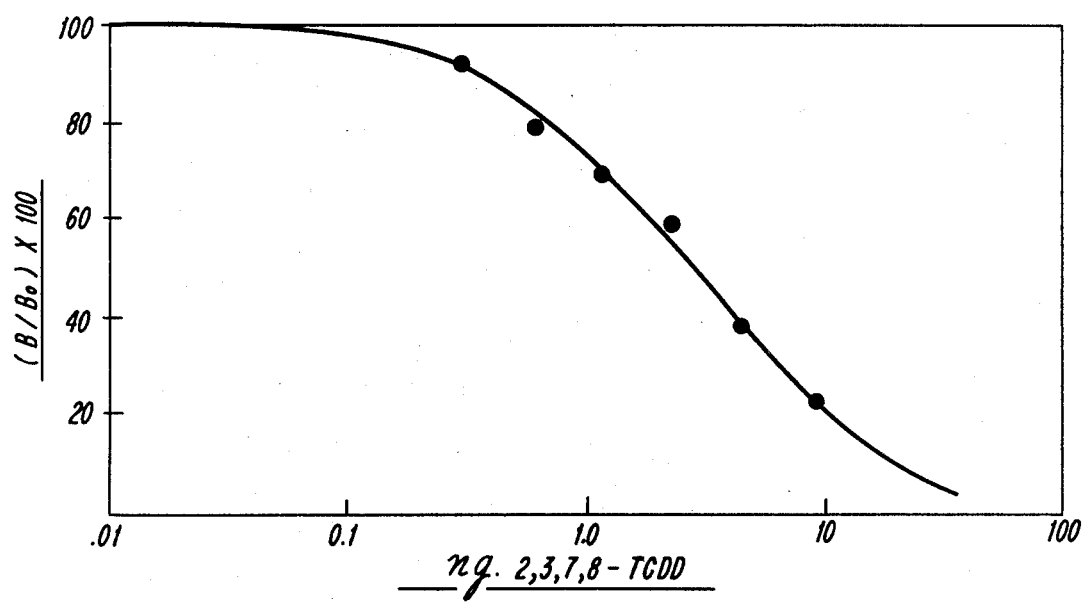

United States Patent [19]

Albro et al.

[11] 4,238,472

[45] Dec. 9, 1980

[54] RADIOIMMUNOASSAY FOR CHLORINATED DIBENZO-P-DIOXINS

[75] Inventors: Phillip W. Albro, Cary; Kun Chae, Durham; Michael I. Luster, Chapel Hill; James D. McKinney, Raleigh, all of N.C.

[73] Assignee: United States of America, Washington, D.C.

[21] Appl. No.: 963,784

[22] Filed: Nov. 27, 1978

[51] Int. Cl.² .................... G01N 33/16; A61K 43/00
[52] U.S. Cl. ................................ 424/1; 23/230 B; 424/12
[58] Field of Search .................. 424/1, 1.5, 12; 23/230 B

[56] References Cited

U.S. PATENT DOCUMENTS

| | | | |
|---|---|---|---|
| 3,241,920 | 3/1966 | Zweig | 23/231 |
| 3,896,217 | 7/1975 | Johnson | 424/1 |
| 3,897,212 | 7/1975 | Leon et al. | 23/230 B |
| 3,985,867 | 10/1976 | Redshaw | 424/1.5 |
| 4,022,876 | 5/1977 | Anbar | 424/1 |
| 4,022,878 | 5/1977 | Gross | 424/1.5 |

*Primary Examiner*—Benjamin R. Padgett
*Assistant Examiner*—Christine M. Nucker

*Attorney, Agent, or Firm*—Holman & Stern

[57] ABSTRACT

The invention provides a double-antibody radioimmunoassay method for the determination of chlorinated dibenzo-p-dioxins, particularly, 2,3,7,8-tetrachlorodibenzo-p-dioxin, in environmental samples including animal tissues such as monkey liver and adipose tissues. The limit of detection is approximately 25 picograms for 2,3,7,8-tetrachlorodibenzo-p-dioxin. Assuming an appropriate cleanup procedure is used, chlorinated dibenzofurans are the only likely interferences, and these can be distinguished through the use of two antisers of different dibenzo-furan/dibenzodioxin selectivities. The invention includes the preparation of a reproducible antigen, an appropriate radiolabeled hapten, and effective sample extracts. A feature of the assay method is the use of a nonionic detergent (e.g., "Cutscum" or "Triton X-305") to solubilize the extremely hydrophobic dibenzo-p-dioxins in a manner permitting their binding by antibodies. The immunoassay is applicable to screening samples in order to minimize the demand for mass spectrometric screening, and to routine monitoring for exposure to known chlorinated dibenzo-p-dioxins in potentially contaminated environments.

13 Claims, 2 Drawing Figures

RADIOIMMUNOASSAY FOR CHLORINATED DIBENZO-P-DIOXINS

The assay method for determining the amount of a chlorinated dibenzodioxin contaminant in an environmental sample (such as liver and adipose tissues) involves removing all naturally-occurring lipids and water-soluble components that might interfere with the subsequent assay from the environmental sample to obtain a final sample containing the chlorodibenzodioxin, emulsifying the final sample with a detergent (such as "Cutscum" or "Triton X-305"), incubating the detergent emulsion with anti-chlorinated dibenzodioxin serum and a $^{125}$I-labeled chlorinated dibenzodioxin derivative (hapten) to obtain a mixture containing a formed antibody -$^{125}$-I-labeled dioxin association complex, adding a second antibody (such as goat anti-rabbit γ-globulin) to precipitate the antibody -$^{125}$-I-labeled dioxin complex, and determining the amount of radioactivity in the precipitate and comparing it to a standard curve to determine the amount of the chlorinated dibenzodioxin present in the sample. The assay is particularly applicable to the determination of the concentration of 2,3,7,8-tetrachlorodibenzo-p-dioxin in the environmental sample.

The invention relates to a rapid and convenient double-antibody radioimmunoassay method for determining the concentration of pollutants comprising chlorinated dibenzo-p-dioxins (hereinafter referred to as "CDBD's"), particularly 2,3,7,8-tetrachorodibenzo-p-dioxin (herein referred to as "TCDD") in environmental samples, including animal tissues such as monkey liver and adipose tissues.

The present invention provides the only presently available alternative to mass spectrometry. Only a very few (less than 10) laboratories in the United States are able to do part-per-trillion analyses for CDBD's, particularly TCDD, by mass spectrometry, and there is no presently available method to confirm their results. The present invention would permit such analyses to be performed in any clinical laboratory presently capable of doing radioimmunoassays, and, in addition, provides a relative inexpensive screening assay for CDBD's, particularly TCDD, that can be used to confirm mass spectral identification of this substance.

Since the antiserum used in the inventive method is employed in high dilution, one milliliter of it will perform over 10,000 assays.

Also, other compounds usually found in association with CDBD's, particularly TCDD, such as polychlorinated biphenyls (hereinafter referred to as "PCB's"), plasticizers, chlorinated phenols, herbicides, etc., do not interfere.

The lower limit of quantitative sensitivity of the assay is about 100 picograms of TCDD.

BACKGROUND OF THE INVENTION

The chlorinated dibenzo-p-dioxins (CDBD's) are a class of widespread environmental pollutants of considerable current concern. They occur as contaminants in commercial chlorophenols and especially as side products of the manufacture of chlorophenoxyacids. The main chlorodibenzo-p-dioxin found as a contaminant of the popular herbicide 2,4,5-trichlorophenoxyacetic acid (hereinafter referred to as "2,4,5-T") is 2,3,7,8-tetrachlorodibenzo-p-dioxin (TCDD), possibly the most toxic man-made chemical known. This compound has an acute oral LD$_{50}$ of less than 1 microgram per kg in the guinea pig. Exposure of humans to this toxin has occurred inadvertently through the use of 2,4,5-T-contaminated waste oil and through industrial accidents such as the explosion of a manufacturing plant utilizing trichlorophenol in Sevesco, Italy in 1975. The defoliant mixture "Agent Orange", disseminated in vast quantities in Vietnam during the 1960's also contained a significant amount of TCDD.

TCDD is not the only highly toxic chlorinated dibenzo-p-dioxin. The 1,2,3,7,8-pentachloro-, 1,2,3,6,7,8-hexachloro- and 1,2,3,7,8,9-hexachloro isomers have toxicities comparable to that of TCDD, and only a few of the possible isomers have thus far undergone toxicity testing.

Until recently, the only analytical technique with sufficient sensitivity and specificity for determination of TCDD has been high resolution mass spectrometry [as described by R. Baughman et al in an article entitled "An Analytical Method for Detecting TCDD (dioxin) Levels of TCDD in Samples from Vietnam". *Environ. Health Persp.*, 5,27–36,(1973)]. Gas chromatography combined with low or medium resolution mass spectrometry in either electron impact or chemical ionization modes [as described by J. R. Hass et al in an article entitled "Determination of Polychlorinated Dibenzo-p-Dioxins in Biological Samples by Negative Chemical Ionization Mass Spectrometry." *Anal. Chem.* 50/11, 1474–1479 (1978)] has been used recently to estimate levels of chlorodibenzo-p-dioxins (CDBD's) in addition to TCDD itself. The detection limits of these techniques are on the order of a few tens of picograms when the samples are free of interfering contaminants.

Because of the cost and complexity of gas chromatography-mass spectrometry instrumentation and the high degree of skill and experience needed in assays of this type, only a few laboratories are able to perform CDBD assays at the present time. This situation has resulted in a slow output of analytical data. Additionally, the lack of a confirmatory technique not based on mass spectrometry has tended to limit the confidence of those not trained in that specialty in the data presently available. For these reasons, the present inventors have developed an assay based on the highly sensitive and relatively specific technique of radioimmunoassay. They believe that this assay will be applicable both to screening samples to minimize the demand for mass spectrometric analysis by eliminating "negatives", and for routine monitoring of exposure in environments where specific CDBD's are known to be present.

SUMMARY OF THE INVENTION

In general, the invention provides a method of determining the concentration of a chlorinated dibenzo-p-dioxin (CDBD) pollutant, in an environmental sample, such as monkey liver and adipose tissues. The method involves the steps of preparing a sample containing the CDBD, reacting it with a first antibody comprising an anti-CDBD serum (i.e., blood serum containing antibodies which bind CDBD) and a radioactive labeled $^{125}$I-CDBD derivative to form an antibody-$^{125}$I-labeled dioxin association complex, reacting the complex with a second antibody, such as goat anti-rabbit gamma globulin, to obtain a precipitate containing the CDBD, assaying the radioactivity in the precipitate, and comparing it to a standard curve to determine the amount of CDBD in the sample.

The present invention has three aspects that are novel, namely:

1. The use of adipamide side chains to give strong determinant activity to the chlorinated dibenzo-p-dioxin moiety in synthesizing the antigen (as described under "B", "E", and "F" of "Methods" hereinafter). This use, incidentally, is not restricted to the dioxins, as the inventors have also successfully employed it with polychlorinated biphenyls and chlorinated biphenyl ethers.

2. The use of a detergent, which, to be effective, must solubilize up to one microgram of hapten per ml of water, must not itself inhibit the binding of the hapten to the antibody by more than 10% at the concentration of detergent needed for solubilization, and must not interfere with precipitation of the antibody-hapten complex by the second antibody even over a one-week incubation period. Such detergents, which the inventors have found to be operative, have the general formula:

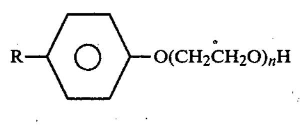

wherein R is any normal or branched alkyl group, particularly the 1,1,3,3-tetramethylbutyl group, and n≧8. The inventors have found only two detergents to be operative, namely, "Cutscum" in which the mean value of n=8, and "Triton X-305" in which the mean value of n=30.5, with the R group in both of these detergents being the 1,1,3,3-tetramethylbutyl group. Other detergents tested, namely, "Tergitol", "Brij", "Zonyl FS", "Tween 20" and "Tween 80", were found to be inoperative.

3. This is the first radioimmunoassay for the chlorinated dibenzo-p-dioxins, particularly TCDD.

Since TCDD exemplifies the most important of the CDBD contaminants, the invention will be described hereinafter with particular reference to this substance.

The following methods were employed in carrying out the invention.

A. General Principle of the Assay

Since TCDD itself has no chemically reactive functional groups, a derivative was synthesized that retained most of the structural features of TCDD but with the addition of a reactive site. This derivative was coupled to an immunogenic protein carrier, such as bovine serum albumin, rabbit serum albumin, etc., so that animals would respond to it by producing an antiserum containing antibodies. A second compound was synthesized, still structurally similar to TCDD so that it would bind to the antibodies, but capable of being labeled with $^{125}I$ for detectability at the picogram level. An amount of antiserum capable of binding about 20 pg of $^{125}I$-labeled dioxin derivative (hapten) is preincubated with the detergent emulsion of the sample extract (possibly containing TCDD). Then the mixture is incubated with the $^{125}I$-labeled derivative long enough for equilibrium binding to occur and form the hapten-antibody complex. A second antibody, namely, goat antibodies against rabbit gamma-globulin (i.e., goat anti-rabbit γ-globulin) are then added to precipitate the antibody $^{125}I$-labeled dioxin complex, and the amount of $^{125}I$ in the precipitate is determined. The extent to which preincubation with the test material inhibits or decreases the amount of $^{125}I$ precipitated relative to the amount precipitated in the absence of test material is a measure of the amount of chlorodibenzodioxin in the test sample.

B. Synthesis of Antigens

In the following description, "antigen" will refer to protein conjugated with dioxin derivative. "Hapten" will refer to any dioxin derivative not attached to protein but capable of being bound by antibodies raised against the dioxin-protein conjugate. "Determinant" will be used rather loosely to refer to the dioxin moieties attached to the antigen.

Many chlorodibenzodioxin derivatives were tested, as were several coupling reactions; the most reproducible, stable and immunogenic antigens were prepared as follows:

1-Amino-3,7,8-trichlorodibenzo-p-dioxin [synthesized as described by K. Chae et al in "Synthesis of 1-amino-3,7,8-trichlorodibenzo-p-dioxin and 1-amino-2,3,7,8-tetradichlorodibenzo-p-dioxin as haptenic compounds" appearing in Agric.Foods Chem. 25/5,1207–1209 (1977)] was reacted with the acid chloride of mono-methyl adipate in pyridine solvent at 0° overnight. The product was extracted into diethyl ether, washed with 1 N HCl to remove pyridine, then with 0.4 M potassium carbonate to remove acid, washed once with saturated aqueous KCl and dried over anhydrous sodium sulfate. One mmole (444.5 mg) of product was hydrolyzed under reflux for 90 minutes in 22.5 ml of 0.09 M NaOH in 66.7% ethanol. This hydrolysis removed the methyl ester moiety but did not affect the amide bond. The hydrolysate was first extracted with petroleum ether (bp. 30°–60°), then acidified with 1 N HCl and extracted three times with equal volumes of diethyl ether. The ether extract was washed with distilled water and dried over anhydrous sodium sulfate. The structure of the adipamide and absence of detectable impurities was confirmed by gas chromatography-mass spectrometry of the methyl ester, which was generated from a portion of the adipamide by treatment with diazomethane [according to the procedure of Th.K. DeBoer et al in "A New Method for the Preparation of Diazomethane" appearing in *Rec.Trav. Chem Paysbas.*, 73,229–234 (1954)]. The gas chromatography involved a column of 3% OV-on Gas Chrom Q, programmed from 150°–250° at 6°/min. The mass spectrum showed $M^+$ at m/e 436, methyl ester (m/e 74), and an isotope pattern corresponding to three chlorines. The free acid (adipamide) had λmax 302 nm, $\epsilon=3.83\times10^3$ L $cm^{-1}$ $mole^{-1}$ in 0.1 N NaOH, and λmax 238 nm, $\epsilon=2.5\times10^4$ L $cm^{-1}$ $mole^1$ in the same solvent.

The adipamide was converted to a mixed anhydride as follows: 0.06 mmole of adipamide in 2.4 ml of dry, peroxide-free 1,4-dioxane, was treated with 15 μl (0.06 mmole) of tri-n-butyl amine and 8.3 μl (0.063 mmole) of fresh isobutyl chloroformate in that order. After stirring 20 min. at room temperature, all of the reactants had dissolved.

The mixed anhydride preparation was added in one portion to a solution of 0.2 g protein in 5.25 ml of water, 0.2 ml of 1 N NaOH and 4.24 ml of dioxane in an ice bath. After stirring for 1 hour, another 0.1 ml of 1 N NaOH was added. After an additional 3 hour of stirring, the derivatized protein was dialyzed overnight against 2 L of 0.1 N ammonium carbonate. The dialysin was freeze-dried and the resulting powder extracted with 50 ml of chloroform using a Waring blender. The suspension was filtered through Whatman #50 paper, and the conjugated protein dried in vacuo over Carbowax 20 M.

Success in the above procedures required that the pyridine be very dry (freshly redistilled from BaO and stored over NaOH pellets), and the dioxane be passed through a column of neutral alumina to remove peroxides just before use.

C. Characterization of Antigens-Number and Locations of Determinants

The protein content of solutions of albumin [as, for example, bovine serum albumin (hereinafter referred to as "BSA", rabbit serum albumin (hereinafter referred to as "RSA", and human serum albumin (hereinafter referred to as "HSA")], thyroglobulin or antigen was determined by biuret method [as described by B. T. Doumas in "Standards For Total Serum Protein Assays—A collaborative Study"., appearing in *Clin. Chem.* 21/8, 1159–1166,(1975)]. The number of free amino groups was determined by the ninhydrin assay [according to the method described by V. J. Harding et al in "Estimation of Amino Groups with Ninhydrin", appearing in J.Biol. Chem. 24, 503–517 (1916)] and confirmed using trinitrobenzene sulfonate [as described by L. C. Mokrasch in "Use of 2,4,6-Trinitrobenzene-Sulfonic Acid for the Coestimation of Amines, Amino Acids, and Proteins in Mixtures", appearing in *Anal. Chem.* 18/1,64–61 (1967)]. Free-OH of tyrosyl units was determined using the Folin-Ciocalteu phenol reagent [as described by A. E. Kabat et al, in *Experimental Immunochemistry.* Charles C. Thomas, Springfield, Illinois, 2nd Ed., 556–557 (1961)]. When the protein was dissolved in 20% $Na_2CO_3$, tryptophan did not interfere (both ribonuclease, with no tryptophan, and avidin, with 4.82% tryptophan and only 0.74% tyrosine, gave the correct apparent amount of phenolic-OH). Tryptophan was measured in the unhydrolyzed protein [according to the method described by M. K. Gaitonde et al in "A Rapid and Direct Method for the Quantitative Determination of Tryptophan in the Intact Protein", appearing in *Biochem. J.* 117/5, 907–911 (1970)].

As long as the protein was kept free of moisture during the extraction with chloroform, it remained undenatured. Attempts to extract antigen in aqueous solution produced extremely insoluble protein precipitates.

D. Immunization

New Zealand White rabbits were immunized on a wide variety of schedules. The most effective procedures were either to give weekly injections of a mixture of 10 mg antigen per ml in Tyrode's solution with an equal volume of Freund's complete adjuvant (sonicated before use, given intramuscularly, incomplete adjuvant substituted after the first booster shot), or to give intradermal injections at multiple sites of a total of 2 mg of antigen in 0.5 ml of physiological saline emulsified in 1 ml of complete Freund's adjuvant. Weekly intramuscular booster shots (1 mg of antigen) were continued until a maximum primary response was obtained. The primary antibody response plateaued after 3 months, was allowed to decay, and a secondary response was induced by injecting 1 mg of antigen intramuscularly in complete Freund's adjuvant. Serum was stored frozen at −70° in small portions, and never re-frozen after a portion was thawed for use.

E. Synthesis of $^{125}I$-labeled Hapten

1-Amino-3,7,8-trichlorodibenzo-p-dioxin was converted to an amide with 5-bromovaleryl chloride as described above for the adipamide derivative. This product (methane chemical ionization mass spectrum: m/e 492=M+29, 464=M+1, 384=M−79) was dissolved in dry acetone (7.5 mg/ml) and treated with enough sodium iodide (17 Ci/mg, low pH) to give 2.5 mg of NaI/ml, at 50° for 20 hours. Diethyl ether was added, and the reaction mixture washed with 10% aq. sodium metabisulfite, then with water. The ether phase was dried over anhydrous sodium sulfate, after which the solvent was evaporated. The crude product, 17 mg, was chromatographed on a 1×25 cm column containing 7 g of activated silica gel. After a benzene wash (100 ml), the iodovaleramide derivative was eluted with 100 ml of 10% chloroform in benzene. It gave a single spot (Rf 0.6) on a silica gel TLC plate with benzene as solvent. The methane-supported chemical ionization mass spectrum showed m/e 540=M+29, 512=M+1, 384=M−127.

Unlabeled 1-N(5-iodovaleramido)-3,7,8-trichlorodibenzo-p-dioxin was dissolved in 100 µl of dry acetone and injected into a vial containing 5 mCi of carrier-free $^{125}I$-sodium iodide. The mixture was held at 50° for 60 hours in a sand bath. After cooling, the products were taken up in 10 ml of chloroform, washed with 10% sodium metabisulfite and water and dried over anhydrous sodium sulfate. The crude product was passed through silica gel (silicic acid) in chloroform to remove traces of unbound iodine. The final product contained 98% of its radioactivity in a single spot during thin layer chromatography on silica gel in benzene, and had a specific radioactivity initially of 78 Ci/m-mole.

F. Absorption of Antisera

In order to select for antisera specific for the dibenzodioxin structure, aniline was converted to an adipamide derivative under the conditions described above, and the adipamide was coupled to bovine serum albumin via the mixed anhydride using isobutyl chloroformate. The protein conjugate was in turn coupled to cyanogen bromide-activated Sepharose 48, which consists of bearded agarose gel treated with CNBr to permit direct covalent coupling of macromolecules containing amino groups, [according to the procedure of P. Cuatrecasas et al described in "Selective Enzyme Purification by Affinity Chromatography", appearing in *Proc. N. A.S.* 61,636–643 (1968)]. Antisera were passed through this affinity column packing with 0.01 M Tris/0.1 M NaCl pH 7.4 as eluant, dialyzed against the same buffer, and concentrated to the original volume by vacuum dialysis. This procedure removed antibodies recognizing the adipamide linkage. Antibodies to the adipamide linkage were later eluted from the immunoabsorbent with 3 M NaSCN in Tris buffer.

G. Tissue Extraction and Cleanup

Tissues (liver, adipose, serum) were processed to prepare the sample [according to the method of Albro et al in "Extraction and Clean-up of Animal Tissues for Subsequent Determination of Mixtures of Chlorinated Dibenzo-p-Dioxins and Dibenzofurans", appearing in *Chemosphere* 7/6, 381–385 (1977)]. Soil samples should be extracted with acetone in a Soxhlet extraction apparatus [as described by G. Seidl in "Isolation of PCB's From Soil; Recovery Rates Using Different Solvent Systems", appearing in *Chemosphere* 5,373–376 (1976)] and the extracts purified as for tissue extracts (Albro et al,supra). The final residues, in small volumes of benzene, were dried under a nitrogen stream in disposable assay tubes. To each tube was added 200 µl of 1%"Cutscum" or "Triton X-305" ("Cutscum" unless otherwise specified below) in methanol, and the solvent was again blown off with nitrogen.

The preparation of the environmental sample containing the TCDD contaminant (e.g., liver and similar tissues, blood, urine, milk, serum, and adipose tissue) for use in the assay technique of the invention, is described in greater detail as follows:

1. The Extraction and Preliminary Clean-up [according to the method described by Albro et al supra, i.e., in *Chemosphere* 7/6, 381–385 (1977)] is carried out as follows:

A. Extraction:

Liver and similar tissues:

Blend 10 g of tissue in 200 ml of chloroform:methanol, 2:1 (v/v). Filter with suction through glass fiber filter paper (Reeve Angel grade 934AH or equivalent). Return the filter paper and cake to the blender jar and blend with 100 ml of chloroform:methanol, 2:1 (v/v). Filter as above ad combine filtrates. Add 52 ml of 1.2% aqueous KCl, mix well, let phases clear, and collect the lower phase in a 500 ml round bottom flask. Evaporate just to dryness at 40° using a rotary evaporator and water aspirator. This is a modification of the method of Folch et al [*J.Biol.Chem.*,236,497 (1957)].

Blood, urine, milk, serum:

Extract as described by Kates [*Techniques of Lipidology* p.351, Elsevier, N.Y.(1972)], using his modification of the procedure originally described by Bligh and Dyer [*Can.J.Biochem. Physiol.*, 37, 911 (1959)]. Again, condensate the chloroform phase using a rotary evaporator.

Adipose tissue:

Grind together 8 g of anhydrous sodium sulfate per gram of adipose, using a mortar and pestle. Extract the resulting powder with chloroform in a Soxhlet extractor, allowing at least 8 cycles.

B. Preliminary Clean-up:

Leach the lipid residue from 10 g of liver, 100 ml of blood or 1 g of adipose into 15 ml of $CCl_4$. Partition against 15 ml of con.$H_2SO_4$. Centrifuge at 2000 rpm for 30 minutes. Remove as much of the $CCl_4$ layer as possible and record the volume recovered. Pass the $CCl_4$ solution through anhydrous $Na_2CO_3$ in a glass wool-plugged funnel, rinising the $Na_2CO_3$ with 2 ml of fresh $CCl_4$. Concentrate the filtrate just to dryness on a rotary evaporator at 40°. Leach the residue into 1.5 ml of n-hexane:methylene chloride, 97:3 (v/v).

2. The lipid extract, obtained in Step 1 above, is subjected to gel permeation chromatography utilizing a modified mini-alumina column system to separate the lipids from the pesticide fraction [in accordance with the procedure described in a brochure, dated May 8, 1978, from the manufacturer of the chromatograph (Analytical Bio Chemistry Laboratories, Inc., P.O. Box 1097, Columbia, Missouri 65201) and entitled "Application Note 1- Modified Procedure for Nonionic Chlorinated Pesticides Prepared for Analysis by Gel Permeation Chromatography"].

3. The separated pesticide fraction is thereafter subjected to emulsifier sonication to produce the final sample for the assay procedure of the invention. This final sample, generally, is an enriched "concentrate" containing the chlorinated dibenzo-p-dioxin (e.g., TCDD) originally present in the environmental sample to be analyzed and from which all water-soluble components and all naturally-occurring lipids that might interfere in the assay have been removed. The sonication was carried out in the sonic bath manufactured by Heat Systems Ultrasonics, Inc.

H. Assay Procedure

Radioimmunoassay of small molecules requires some means of separating free hapten from antibody-bound hapten. The procedure used in the present invention, chosen because of its compatibility with detergent-solubilized hapten, involved precipitating the antibody-hapten complex with a second antibody, namely, goat antibodies against rabbit gamma-globulin. In this assay chlorodibenzodioxin from the environmental sample completes with the $^{125}I$-labeled hapten for binding to the antibody. Thus, the decrease in precipitation of radioactivity is a measure of the amount of (unlabeled) hapten in the test sample.

The assay buffer (hereinafter referred to as "PBS") contained, per liter, 20 mmol of potassium phosphate, 140 mmol of NaCl, and 200 mg of sodium azide. The pH was adjusted to 7.3 with NaOH. Antiserum was diluted with PBS also containing 0.1% bovine gamma globulin and 0.02% rabbit gamma globulin (w/v). Each assay tube from procedure G above received 0.2 ml of PBS, after which the tubes were held in the sonicator for 40 minutes and then cooled to room temperature. Appropriately diluted antiserum or, as control, antiserum diluant was added (0.2 ml) and, after vortex-mixing, the tubes were incubated for 40 minutes at 37°. 14000 disintegrations per minute (hereafter referred to as "DPM") or 7000 counts per minute (hereinafter referred to as "CPM", which equals DPM×counting efficiency) of [$^{125}I$]-iodovaleramide derivative of trichlorodibenzo-p-dioxin in PBS containing 1% "Cutscum" were then added to each tube (approximately 10 μl), vortex mixed, and the tubes incubated for 1 hour at 37° followed by an additional 65 hours of incubation at 4°. Each tube next received 1.24 units of goat anti-rabbit gamma globulin in 0.2 ml of PBS containing 0.05 mM ethylenediamine tetracetic acid (hereinafter referred to as "EDTA"), was vortex mixed, and incubated for 5 hours at 4°. The tubes were centrifuged at 500×g for 20 minutes at 4°. The supernates were poured off and the tubes allowed to drain into Whatman #3 MM paper for 10 minutes. The precipitate or pellets obtained were then radioassayed for $^{125}I$, with 10 minute count cycles.

Standard curves were prepared using sequential two-fold dilutions of TCDD or other test compounds in benzene and evaporating the solvent as described above. Both control (blank) and TCDD-spiked tissues were extracted and processed as described above to determine general interference and recoveries. All samples were run in triplicate.

Incubation times required for maximum, reproducible binding were determined from time/temperature studies. General methods for optimizing the conditions for the double-antibody separation system have been described [as see W. B. Hunter, *Handbook of Experimental Immunology*, D. M. Weir, Ed., Blackwell Scientific Publ., Oxford, England, Chap. 17, 1–36 (1973)]. Nonspecifically bound and precipitated radioactivity was, in these detergent-containing systems, quite minor and reproducible, so that radioactivity in pellets of tubes lacking anti-CDBD anti-serum could simply be substracted from the radioactivity in assay tubes.

Calibration curves were obtained by plotting $(B/B_o) \times 100$, where B represents CPM in tubes containing unlabled affector (calibration standard, unknown, or inhibitor) and $B_o$ represents CPM in the tubes lacking affector, against amount of unlabeled affector or semilog paper [as described by M. I. Luster et al in "Radioimmunoassay for Mono-(2-ethylhexyl) Phthalate in Unextracted Plasma", appearing in *Clin. Chem.* 24/3, 429–432 (1978)]. In the case of 2,3,7,8-tetrachlorodibenzo-p-dioxin, a linear calibration curve could also be obtained for antiserum GC-5 by plotting percentage inhibition against the $\log_{10}$ of the TCDD concentration.

RESULTS AND DISCUSSION

Preliminary experiments revealed that the mixed anhydride coupling procedure described above gave a reproducible degree of conjugation, with 80±2% of the hapten moiety being covalently bound to protein over a range from 10–50 moles anhydride per mole of protein. This coupling was relatively independent of the hapten moiety, as long as an adipamide side chain was used. Thus, we have prepared antigens containing bound amino-tetrachlorobiphenyls, aminochloribiphenyl ethers, and other substituted aniles by this method with equal success.

UV difference spectra, with antigen protein concentration made equal to the corresponding unconjugated protein concentration on the basis of biuret assays, provided a measure of bound plus adsorbed hapten. In all cases considered here, adsorbed hapten could be separated from the conjugated protein by chromatography on Sephadex G-100 (purified dextran gel polymer in bead form having pores about the size of a globular protein of molecular weight 100,000 Daltons and smaller); no adsorbed hapten could be detected if the freeze-dried antigen had been extracted with chloroform. Under these circumstances, total hapten associated with protein (by UV difference spectrum) agreed with the sum of the decreases in amino and phenolic hydroxyl groups of the protein.

The BSA-based antigen used in this study had, on the average, 10.75±0.15 (S.D.) moles of trichloridibenzo-p-dioxin coupled at the γ-amino group of lysine and 3.3±0.1 (S.D.) moles coupled at tyrosine, per mole of protein (assuming mol. wt. BSA=67000). Thyroglobulin bound 77±3 moles of the dioxin at lysine and 20±1 moles at tyrosine, per mole of protein (assuming a mol. wt. of 670,000 for calf thyroglobulin). Rabbit serum albumin, mol. wt. 67000 assumed, bound 12 moles of hapten per mole of protein, with a distribution similar to that of BSA. Neither antigen showed a decrease in trypophan as assayed in the intact protein according to (Gaitonde et al, supra).

Six rabbits were immunized with the dioxin derivative of thyroglobulin and seven with the derivative of BSA. All 13 rabbits produced antisera which gave precipitin lines (double immunodiffusion) with the dioxin conjugate of RSA, but not with RSA alone. At least one of the rabbits immunized with the thyroglobulin conjugate produced antibodies specific for the linkage unit, in that all detectable binding to the dioxin-RSA conjugate was eliminated by passing the antiserum through the aniline-adipamide-BSA-Sepharose a affinity columns. Other antisera were apparently specific for the dioxin moiety, in that their titres did not change on passage through the affinity column. Still other antisera were intermediate.

The development of the radioimmunoassay passed through several stages, in which fluorescein-conjugated, trichlorodibenzo-p-dioxin-1-adipamide conjugated BSA and later $^{125}$I-labeled, trichlorodibenzo-p-dioxin-1-adipamide conjugated RSA were used as assay reagents. The latter procedure was described briefly in abstract form [P. W. Albro et al, "Radioimmunoassay for 2,3,7,8-tetrachlorodibenzo-p-dioxin", appearing in *Environ. Health Persp.* 20,244 (1977)]. In the course of these previous studies, antisera were selected on the bases of high specificity toward chlorinated dibenzo-p-dioxins, low recognition of the linkage arm, and high affinity for the dioxin moiety. Antisera showing inability to bind at least 95% of 40 pg of $^{125}$I-labeled 1-N(5-iodobaleramido)-3,7,8-trichlorodibenzo-p-dioxin were rejected. For the experiments discussed here, two antisera designated GC-5 and F-12 were selected for detailed evaluation. The former was raised against the thyroglobulin conjugate, the latter against the BSA conjugate.

Fifteen detergents were compared as to their ability to solubilize TCDD without interfering seriously with the antibody-hapten interaction. Only two, having the general formula

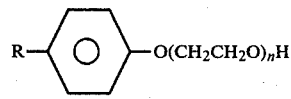

wherein R is any normal or branched alkyl group, particularly the 1,1,3,3-tetramethylbutyl group, and $n \geq 8$, and exemplified by "Triton X-305" (wherein the mean value of n=30.5) and "Cutscum" (wherein the mean value of n=8), with the R group in both of these detergents being the 1,1,3,3-tetramethylbutyl group, were found suitable. To be acceptable, a detergent must solubilize up to one microgram of hapten per ml of water, must not itself inhibit the binding of the hapten to the antibody by more than 10% at the concentration of detergent needed for solubilization, and must not interfere with precipitation of the antibody-hapten complex by the second antibody even over a one-week incubation period. The others (various Triton, Tween, Brij, Tergitol and Zonyl synthetic detergents, bile salts, etc.) either did not solubilize TCDD, solubilized it but "shielded" it from the antibody, or interacted strongly with the antisera proteins. Typical standard curves for inhibition of the binding of the radioiodinated hapten to the antibody by TCDD in the presence of "Cutscum" or "Triton X-305" are shown in the accompanying FIGS. I and II. A lower level of TCDD could be measured using "Triton X-305" than using "Cutscum", but a wider range of concentration could be assayed using "Cutscum" than using "Triton X-305".

Cross reactivity was elevated in the assay using "Cutscum". The following Table 1 gives an indication of the possible interference to be expected from compounds other than chlorodibenzo-p-dioxins.

TABLE 1

| Specificity of the Radioimmunoassay[a] | | |
|---|---|---|
| Compound | Highest Amount Tested | Percentage Reactivity |
| 3,4,3',4'-TCBP[c] | 5 ng | 6 |
| 2,6,2',6'-TCBP | 200 ng | 0 |
| 3,5,3',5'-TCBP | 100 ng | 0 |
| 3,4,5,3',4',5'-HCBP | 100 ng | 0 |
| 2,4,5,2',4',5'-HCBP | 100 ng | 0 |
| Aroclor 1254 | 1 μg | 0 |
| 3,4,3',4'-TCBPE | 200 ng | 0.1 |
| DEHP | 100 μg | 0 |
| Tetrachloro DEHP | 200 ng | 0.1 |

TABLE 1-continued

Specificity of the Radioimmunoassay[a]

| Compound | Highest Amount Tested | Percentage Reactivity |
|---|---|---|
| Anthracene | 100 ng | 0 |
| α-Tocopherol Acetate | 200 ng | 0 |
| DDE | 400 ng | 0 |
| 9-Fluorenone | 100 ng | 0 |
| 2,7-Dichlorofluorescein | 200 ng | 0 |
| Pentachlorophenol | 10 μg | 0 |
| 2,4,5-T (Commercial) | 10 μg | 37 |
| Cholesterol Oleate | 100 μg | 0 |

[a] Using antiserum F-12 and "Cutscum". Amounts testable depended upon "solubility" in 1% "Cutscum".
[b] Percentage inhibition of $^{125}$I-binding by maximum anount of test substance relative to percentage inhibition by 5 ng of 2,3,7,8-TCDD.
[c] TCBP = tetrachlorobiphenyl; HCBP-hexachlorobiphenyl; DEHP = di-(2-ethylhexyl) phthalate; TCBPE = tetrachlorodiphenyl ether.

The potential for interference in this assay is somewhat self-limiting, since only those amounts of hydrophobic compounds capable of being solubilized in 1% "Cutscum" are actually presented effectively to the antibodies. Thus, while commercial polychlorinated biphenyl (hereinafter referred to as PCB) mixtures do contain traces of 3,4,3'4'-tetrachlorobiphenyl and chlorinated dibenzofurans which cross react, only about 5 μg of total ∓Arochlor" (a commercial mixture of polychlorinated biphenyls) can be accommodated in 0.2 ml of 1% "Cutscum". At this level of "Arochlor", the cross reacting components are at too low concentrations to interfere. In addition, PCB's are removed from the dioxin fraction in the cleanup procedure (Albro et al, supra). The most probable contaminats in a dioxin fraction following the described cleanup are sterol esters, which do not cross react.

The following Table 2 shows the relative cross reactivity of several chlorinated dibenzo-p-dioxins (hereinafter referred to as "DBD's") and dibenzofurans (hereinafter referred to as "DBF's") using two of the antisera.

TABLE 2

Cross Reactivity in Chlorinated DBD Assay

| | Cross Reactivity[a] | |
|---|---|---|
| | Antiserum GC-5 | Antiserum F-12 |
| Dibenzo-p-Dioxin | | |
| Unchlorinated | 4 | <1 |
| 2,3-Cl$_2$ | 44 | 16 |
| 2,7-Cl$_2$ | 56 | 20 |
| 2,8-Cl$_2$ | 52 | 17 |
| 2,3,7-Cl$_3$ | 73 | 77 |
| 1,2,3,4-Cl$_4$ | 20 | <1 |
| 2,3,7,8-Cl$_4$ | 100 | 100 |
| 1,2,3,7,8-Cl$_5$ | 99 | 97 |
| 1,2,4,7,8-Cl$_5$ | 76 | 36 |
| 1,2,3,4,7,8-Cl$_6$ | 99 | 9 |
| 1,2,3,6,7,8-Cl$_6$ | 99 | 9 |
| Octachloro | 100 | 8 |
| Dibenzofuran | | |
| Unchlorinated | 2.5 | <1 |
| 2,8-Cl$_2$ | 12 | ND[b] |
| 2,3,8-Cl$_3$ | 2 | ND[b] |
| 2,3,6,8-Cl$_4$ | 6 | 40 |
| 2,3,7,8-Cl$_4$ | 25 | 92 |
| Octachloro | 14 | 8 |
| 2,3,7,8-Br$_4$ | ND[b] | 46 |

[a] 100 × (Inhibition of $^{125}$I-binding by 4 pmole of test compound)/(Inhibition by 4 pmole of 2,3,7,8-TCDD).
[b] ND = not done.

Although not determinable from the Table, concentration curves revealed that each cross-reacting dioxin gave a different slope, so the relative percentage cross reactivities depend upon the level compared.

When GC-5 antiserum was diluted such that 33% of the label from [$^{125}$I]-1-N(5-iodobaleramido)-3,7,8-trichlorodibenzo-p-dioxin was bound in the absence of competitors, 2,3,7,8-tetrachlorodibenzo-p-dioxin was able to inhibit this binding by up to 97%. In contrast, 2,3-dichloro DBD could only inhibit a maximum of 55% and only up to 18% inhibition could be detected using 1,2,3,4-tetrachloro DBD. With antiserum F-12, the ratio of inhibition by 5 ng of 2,3,7,8-DBF to that of 2,3,7,8-DBD was constant for incubation times between 2 and 65 hours, indicating that, most likely, the "Cutscum" miscelles orient the hapten with the oxygen atom facing the aqueous environment in both cases. The three dichlorodibenzo-p-dioxins (2,3-; 2,7-; 2,8-) were very similar in their cross reactivity at the 5 ng level, but had very different activity v concentration curve slopes, the 2,8-isomer giving the most shallow slope, and the 2,3-isomer giving the steepest sloop with both antisera. As a result, quantiation of chlorinated dibenzo-p-dioxins with this immunoassay requires knowledge as to which isomers are present. The differing degrees of maximum inhibition suggests that each antiserum has a family of antibodies binding the $^{125}$I-labeled hapten. Essentially all of these antibodies (in GC-5) also bind 2,3,7,8-TCDD, while only a portion bind 2,3-dichloro DBD. Since antisera contain a heterogeneous population of antibodies with various binding sites and affinities, a detailed structure:activity study to "visualize" the "binding site" would be meaningless. In the case of F-12, some generalizations can be made, however. The ring system must contain halogen, but the presence of two or more chlorine atoms in peri positions greatly interferes with binding. Either the 1 and 9 or 4 and 6 positions or both sets must lack substitution for effective competition in the assay. The inventors would predict, then, that 1,2,3,7,8,9-hexachlorodibenzo-p-dioxin would, if available for testing, be an effective competitor. On the other hand, only one of the two oxygen atoms appears to be essential for binding in F-12, since 2,3,7,8-tetrachlorodibenzo-p-dioxin and 2,3,7,8-tetrachlorodibenzofuran show approximately the same reactivity. Unchlorinated dibenzo-p-dioxin shows very little cross relativity with either antiserum.

Using spiked, sandy soil samples, the inventors were able to detect 0.7 picomole of 2,3,7,8-TCDD using "Cutsum" and either antiserum. With "Triton X-305" replacing the "Cutscum", as little as 0.08 picomole of 2,3,7,8-TCDD could be detected. These levels of sensitivity required that a dilution of antiserum (usually about 1:9000) be used that would bind 33% of the $^{125}$I-labeled hapten. To test the applicability of this assay to tissue samples, the inventors obtained liver and adipose samples from monkeys that had been used in a toxicity study involving 2,3,7,8-TCDD [as described by E. E.McConnell et al in "Toxicity of 2,3,7,8-tetrachlorodibenzo-p-dioxin in Rhesus Monkeys (Macaca muletta) Following a Single Oral Dose", appearing in *Toxicol. Appl. Pharmacol.* 43/1,175–187(1978)]. Sample size ranged from 3 to 50 mg of tissue for the radioimmunoassay, while 200 mg samples were used for comparison assays by gas chromatography with either negative chemical ionization mass spectrometry [as described by J. R. Hass et al in "Determination of Polychlorinated Dibenzo-p-Dioxins in Biological Samples by Negative Chemical Ionization Mass Spectrometry", appearing in *Anal. Chem.* 50/11, 1471–1479 (1978)], or an electron capture detector as measuring device. The results are summarized in the following Table 3.

TABLE 3

Comparison of Three Assay Methods for Determination of 2,3,7,8-TCDD in Monkey Tissue

| Animal[a] No. | Tissue | TCDD,ppb | | |
|---|---|---|---|---|
| | | RIA | GM-MS | GC-EC |
| 373 | Adipose | ND[b] | ND | ND |
| 373 | Liver | ND | — | ND |
| 374 | Adipose | ND | ND | ND |
| 374 | Liver | ND | — | ND |
| 380 | Adipose | 41 | 28 | 87 |
| 380 | Liver | 20 | — | 17 |
| 391 | Adipose | 1800 | 1740 | 1810 |
| 391 | Liver | 94 | — | 30 |

[a]Monkeys 373 and 374 were controls and dosed orally with corn oil alone. Monkeys 380 and 391 were experimental and received a single oral dose of 70 μg/kg or 350 μg/kg TCDD in corn oil, respectively.
[b]ND = none detected.
RIA-Radioimmunoassay as described herein, using antiserum F-12 and "Cutscum".
GS-MS = Gas chromatography with negative ion mass spectrometry.
GC-EC = Gas chromatography with electron capture detector.

Of the three techniques, gas chromatography with an electron capture detector has the greatest potential for interference, and thus can only be trusted to set an upper limit for the amount of TCDD in a sample. In the absence of a suitable internal standard (e.g., $^{37}$Cl-TCDD), the mass spectral technique gives results whose accuracy depends upon how soon the unknown sample was run after preparing the standard curve. In contrast, the unknown and standard curve are run simultaneously in the immunoassay procedure. Considering the many differences in the principles involved in the three assay methods, the agreement of results in Table 3 was very acceptable.

In order to determine whether or not the immunoassay could be used in air monitoring studies, small amounts of 2,3,7,8-TCDD were adsorbed on coarse (6–16 mesh) silica gel, let stand overnight, and extracted with boiling methylene chloride (pesticide grade). Silica gel "fines" interfered with the immunoassay, so it was necessary to evaporate the methylene chloride, redissolve the residue in benzene, and centrifuge. The supernate could be assayed without further cleanup. Quantities of 2,3,7,8-TCDD between 350 pg and 10 ng could readily be determined with a mean recovery of 65%. It was later found that the poor recovery was due to loss of TCDD on the silica gel, which appears to absorb TCDD much more strongly than do either sand or alumina. The inventors are presently working on a more effective procedure for silica gel. In the interim, it appears that a standard curve should be prepared using spiked samples of silica gel, in order to compensate for low recovery.

The limited ability of antiserum GC-5 to discriminate against various chlorinated dibenzo-p-dioxin isomers makes this antiserum useful as a screening reagent for this class of compounds in general. Such a screening assay could be used to reduce the number of samples that must receive the much more tedious mass spectrometric assay. When a single dibenzo-p-dioxin is found to be present or to greatly predominate, the radioimmunoassay using antiserum F-12 can be used to confirm the quantitative data from mass spectral analysis. In addition, the immunoassay can be used alone to monitor exposure to dibenzo-p-dioxin in an environment known to contain a particular isomer, in which case the monitoring results would be presumptive in nature.

Although the inventors can make no estimate at this time as to the likelihood that antisera equivalent is specificity to GC-5 or F-12 can be prepared "on demand" in other laboratories, the high percentage responsive of rabbits to these antigens, the relatively high titres (high dilutability) of the antisera, and the fact that the inventors have observed almost no decrease in titre in up to three years of storage at $-70°$ suggests that it should be possible to perform this assay in many laboratories for the foreseeable future.

FIGURE LEGENDS

FIG. 1: Standard Curves. Determination of 2,3,7,8-TCDD using antiserum F-12 with either "Cutscum" or "Triton X-305".

What is claimed is:

1. A radioimmunoassay method for determining the amount of a chlorinated dibenzodioxin contaminant present in an environmental sample comprising:
    (a) removing all naturally-occurring lipids and water-soluble components that might interfere with the subsequent assay from the environmental sample to obtain a final sample containing the chlorinated dibenzodioxin;
    (b) emulsifying the final sample obtained in step (a) with a detergent having the general formula

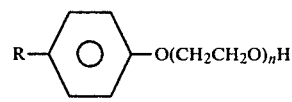

wherein R is a normal or branched alkyl group and $n \geq 8$;
    (c) incubating the detergent emulsion obtained in step (b) with (1) an antiserum containing antibodies to said chlorinated dibenzodioxin and (2) a hapten consisting of an $^{125}$I-labeled derivative of said chlorinated dibenzodioxin capable of being bound by said antibodies, until equilibrium binding occurs, thereby to obtain a mixture containing a formed antibody-$^{125}$I-labeled dioxin association complex;
    (d) adding a second antibody to the mixture obtained in step (c) to precipitate said antibody-$^{125}$I-labeled dioxin complex; and
    (e) determining the amount of radioactivity in said precipitate obtained in step (d) and comparing it to a standard curve to determine the amount of the chlorinated dibenzodioxin present in the sample.

2. The method of claim 1 wherein the chlorinated dibenzodioxin is 2,3,7,8-tetrachlorodibenzo-p-dioxin.

3. The method of claim 1 wherein the environmental sample is a member selected from the group consisting of liver and similar tissues, blood, urine, milk, serum, and adipose tissue.

4. The method of claim 1 wherein the naturally-occurring lipids and water-soluble components are removed by an extraction procedure utilizing a lipid solvent, followed by gel permeation chromatography to obtain a fraction containing the chlorinated dibenzodioxin, which fraction is thereafter subjected to emulsification and sonication to yield the final sample obtained in step (a).

5. The method of claim 1 wherein the detergent employed in step (b) has a mean value of $n=8$ and R is the 1,1,3,3-tetramethylbutyl group.

6. The method of claim 1 wherein the detergent employed in step (b) has a mean value of $n=30.5$ and R is the 1,1,3,3-tetramethylbutyl group.

7. The method of claim 1 wherein the antiserum employed in step (c) is obtained from rabbits immunized by an antigen produced by reacting 1-amino-3,7,8-trichlorodibenzo-p-dioxin with the acid chloride of monomethyl adipate in dry pyridine, hydrolyzing the resulting product to remove the benzyl ester moiety without affecting the amide bond, reacting the resulting adipamide with tri-n-butyl amine and isobutyl chloroformate in that order in dry, peroxide-free 1,4-dioxane to convert the adipamide into a mixed anhydride, and complexing the mixed anhydride with a protein to produce a conjugated protein which serves as the antigen.

8. The method of claim 7 wherein the protein is bovine serum albumin.

9. The method of claim 7 wherein the protein is rabbit serum albumin.

10. The method of claim 7 wherein the protein is bovine thyroglobulin.

11. The method of claim 1 wherein the hapten consisting of an $^{125}$I-labeled derivative of the chlorinated dibenzodioxin employed in step (c) is prepaed by reacting 1-amino-3,7,8-trichlorodibenzo-p-dioxin with 5-bromovaleryl chloride in dry pyridine, hydrolyzing the resulting product to produce the corresponding valeramide, treating the valeramide with sodium iodide to produce unlabeled 1-N(5-iodovaleramido)-3,7,8-trichlorodibenzo-p-dioxin, and reacting this derivative with carrier-free $^{125}$I-sodium iodide to obtain the corresponding $^{125}$I-labeled hapten.

12. The method of claim 1 wherein the second antibody is goat anti-rabbit gamma-globulin.

13. The method of claim 1 wherein the environmental sample consists of soil, silica, or personnel-monitoring patches.

* * * * *